United States Patent [19]

Wysor

[11] 4,020,150
[45] Apr. 26, 1977

[54] ADMINISTRATION OF SILVER SULFADIAZINE AND RADIOACTIVE DERIVATIVES THEREOF

[75] Inventor: Michael S. Wysor, New York, N.Y.

[73] Assignees: Michael Ebert, Mamaroneck; Eugene J. Kalil, New York, both of N.Y.; part interest to each

[22] Filed: Dec. 19, 1974

[21] Appl. No.: 534,288

Related U.S. Application Data

[63] Continuation-in-part of Ser. No. 415,637, Nov. 14, 1973, abandoned.

[52] U.S. Cl. .................................. 424/1; 424/228; 424/290
[51] Int. Cl.² ................. A61K 43/00; A61K 31/63; A61L 13/00
[58] Field of Search ............... 424/1, 228, 229, 290

[56] References Cited

UNITED STATES PATENTS

| 2,422,688 | 6/1947 | Lott | 260/239.75 |
| 3,761,590 | 9/1973 | Fox, Jr. | 424/228 |

OTHER PUBLICATIONS

Sandman et al, Journal of Pharmaceutical Sciences, vol. 63, No. 6, June, 1974, pp. 948–951.

*Primary Examiner*—Benjamin R. Padgett
*Assistant Examiner*—Christine M. Nucker

[57] ABSTRACT

Silver sulfadiazine has been found to be therapeutically useful when administered orally or subcutaneously in doses not exceeding 1,050 mg/kg. It also has been found that radioactive derivatives of silver sulfadiazine localize in tumors, the resultant radiation within the region of the tumor serving to eradicate malignant cells.

4 Claims, No Drawings

ADMINISTRATION OF SILVER SULFADIAZINE AND RADIOACTIVE DERIVATIVES THEREOF

RELATED APPLICATION

This application is a continuation-in-part of the application Ser. No. 415,637 filed Nov. 14, 1973, and now abandoned.

BACKGROUND OF THE INVENTION

This invention relates generally to silver sulfadiazine compositions, and more particularly to the oral or subcutaneous administration of silver sulfadiazine and radioactive derivatives thereof for the treatment of infections and for the eradication of neoplastic tissue.

Anti-bacterial compounds which are known to possess anti-bacterial properties include silver nitrate, the various sulfonamides, such as sulfadiazine, sulfamerazine, sulfanilamide and sulfamylon and the antibiotics, such as the penicillins. The existence of silver salts of p-amino-benzene sulfonamides and their chemotherapeutic activity are also known. U.S. Pat. No. 2,422,688 discloses the preparation of compounds such as silver sulfathiazole, silver sulfanilamide, sulfur sulfadiazine and silver sulfapyridine.

In the Fox U.S. Pat. No. 3,761,590, there is disclosed the fact that silver sulfadiazine and silver sulfadiazine-containing compositions of materials, particularly silver sulfadiazine dispersed in water-dispersible hydrophilic carrier or ointment are especially useful in burn therapy. Broadly, silver sulfadiazine when employed in the treatment of infections in man and animals exhibits anti-bacterial properties, antifungal properties and anti-protozoal properties, e.g., useful in the treatment of trichomonas vaginitis and also exhibits spermicidal activity.

Silver sulfadiazine is stable, insoluble in water, alcohol and ether and does not appear to stain or darken like other silver salts, such as silver nitrate. Silver sulfadiazine, when exposed to body fluids, such as when employed in burn therapy, appears to yield the combined properties of oligodynamic action of silver in addition to the advantages of an antibacterial agent. For example, when silver sulfadiazine is applied in an ointment to burn wounds, the silver sulfadiazine presents the advantages of silver and an anti-bacterial agent without the use of hypotonic solutions and without withdrawing body electrolytes. The silver sulfadiazine appears to react only gradually with the body fluids when used in burn therapy with the result that silver sulfadiazine when employed in burn therapy evidences a sustained active, effective concentration for as long as 24–72 hours after a single application. In contrast, a water-soluble, anti-bacterial agent, such as sodium sulfadiazine, would be used up rapidly and none would be left after a few days. Silver sulfadiazine when used in burn therapy, i.e., when applied to and/or exposed to body fluids, also appears to react with organic sulfahydryl groups or compounds in contact therewith. The disclosure of U.S. Pat. Nos. 2,422,688 and 3,761,590 are herein incorporated and made part of this specification.

The Fox patent is concerned only with the topical applications for silver sulfadiazine, whereas the present invention is based on the discovery that this drug, when administered orally or subcutaneously, is non-toxic and active against various organisms systemically.

DESCRIPTION OF THE INVENTION

I. The Treatment of Infections

Silver sulfadiazine, when administered orally and subcutaneously to CF-1 mice in doses not exceeding 1,050 mg/kg, proved to have minimal toxicity. No pathology or abnormal reactions were seen in CF-1 mice after receiving 1,050 mg/kg orally and subcutaneously once a day for thirty days. Silver sulfadiazine in doses of 1,050 mg/kg, once a day for five days cured mice of P. berghei even after splenectomy. Parasitemia was reduced to zero from one to three days and anti-malarial activity was not inhibited significantly by doses of 313 mg/kg/day of PABA indicating that silver sulfadiazine's anti-malarial mode of action is different from that of the sulfonamides. Doses of 1,050 mg/kg/day had significant activity against systemic infections of P. aeruginosa.

MATERIALS AND METHODS

Drug

Silver sulfadiazine was prepared by reacting equalmolar concentrations of sulfadiazine and silver nitrate. The insoluble reactant was washed until the supernate was silver-free after adding sodium chloride (0.9%) in volumes ten times that of the silver sulfadiazine supernatant. The silver sulfadiazine was washed with acetone and then separate washings of petroleum ether. The precipitate was then placed in a desiccator until all ether had been removed and the precipitate was a dry white, fluffy material. To prepare the drug for administration, it is added to distilled water and shaken vigorously to produce a suspension.

Toxicological Studies

The acute systemic toxicity of silver sulfadiazine was studied by use of various routes of administration in CF-1 mice. Oral tolerance was determined with the material suspended in water and administered by intubation tube and syringe. After an observation period of up to ten days, the $LD_{90-100}$ was determined and the $LD_{50}$ was calculated by the probit method.

For sub-acute toxicity, silver sulfadiazine was administered orally and subcutaneously in one group of mice every day for a month; the second group received the drug every other day for a month. The average weight of the mice was 23.0 grams and the weight gain or loss was monitored during this period. At the end of the month, the animals were sacrificed and sections of kidney, intestine, liver and spleen were removed for histological examination. Tissue sections were fixed in carnoil's solution, and embedded in ester wax: 5 mm thick sections were prepared and stained with hematoxylon-eosin.

Chemotherapeutic Experiments in Mice

The parasite, P. berghei, was maintained in golden hamsters, but all experiments were carried out in mice, 0.2 ml of infected hamster blood with a 10–20% parasitemia was administered to each mouse. Blood smears (from the tail) were taken daily with an infection of 10–20% being reached usually within 7–10 days. At this point the drug was administered in various dosing schedules with smears taken daily. In those animals remaining free of infection for 30 days, splenectomy was performed and the animals were watched for another 30 days. Those animals remaining free of infection after this time were considered cured. For some of these experiments, sulfadiazine and PABA were administered as controls.

Clinical isolates of Ps. aeruginosa were obtained and grown to 18/h broth cultures. 0.2 ml of this trypticase-soy broth pseudomonas culture was administered by intraperitoneal injection. The drug was administered orally 30 minutes after bacterial infection with subsequent doses at 24-hour intervals. The survival rates were determined on the fifth day after infection. Heart's blood cultures were made of all the animals that died.

RESULTS

Acute Systemic Toxicity

Silver sulfadiazine was toxic when administered in doses ranging from 550 to 1,050 mg/kg by intraperitoneal administration. Death occurred within twenty-four hours. Doese of 1,050 mg/kg when administered by oral and subcutaneous routes were not toxic. In these animals receiving the drug subcutaneously, there was evidence of a local reaction.

Subacute Toxicity

No deaths occurred within the two experimental groups by both routes of administration during the 30-day test period. At the end of the test period, all the animals were sacrificed and tissue sections sent to the Department of Pathology for analysis. Histological studies showed that there was no obvious pathology in any of the groups receiving silver sulfadiazine for the test period. There was no weight loss in any of the groups and no evidence of behavioral changes. None of the animals exhibited diarrhea. Those animals receiving the drug subcutaneously had granulomatous lesions at the site of injection, but no pathological changes in the organs examined.

Chemotherapeutic activity against P. berghei (malaria)

When silver sulfadiazine was administered orally to mice bearing P. berghei infections ranging from 9.2% to 12.5%, a drop in parasitemia to 0% (tail smear) was achieved within two days. Doses of the drug were administered in groups of three, four, and five days consecutively. It was found in this experiment that four doses were sufficient to eradicate the infection even after splenectomy.

In the second experiment, various oral doses of silver sulfadiazine were able to inhibit the infection for ten days with five consecutive doses achieving the greatest inhibition.

When silver sulfadiazine was administered by oral and subcutaneous administration for five consecutive days, suppression of the infection to 0% parasitemia was achieved within one day and complete cure was achieved even after splenectomy.

Since both sulfadiazine and silver sulfadiazine have equal efficacy against P. berghei, high doses of para-aminobenzoic acid (PABA) were administered as controls to both sulfadiazine and silver sulfadiazine animals. If the mode of action of silver sulfadiazine against P. berghei was similar to that of sulfonamides, the high doses of PABA should have significantly inhibited its activity. It was found that sulfadiazine was significantly inhibited by PABA, whereas silver sulfadiazine was insignificantly inhibited by PABA according to the protocol of Rollo.

Chemotherapeutic activity against systemic P. aeruginosa infections in mice

At high doses of 1,050 mg/kg, silver sulfadiazine proved effective against Ps. aeruginosa systemic infections as indicated by Table I below:

Table I.

Acute and Subacute Toxicity and in vivo activity against Pseudomonas aeruginosa

I. Acute Toxicity
$LD_{90-100}$ (mg/kg)

| per os | subcutaneous | intraperitoneal |
|---|---|---|
| ≥ 1,050 | ≥ 1,050* | ≥ 550 |

II. Sub-acute Toxicity
LD 900–100 (mg/kg)

| per os | subcutaneous |
|---|---|
| 1,050 | 1,050 |

III. Anti-bacterial activity (Pseudomonas) in vivo
(based on 50 CF-1 mice)

| | per os | subcutaneous |
|---|---|---|
| | (number of animals) | |
| controls | 25 | 25 |
| survivors | 0 | 0 |
| % mortality | 100 | 100 |
| experimental | 25 | 25 |
| survivors | 25 | 19 |
| % mortality | 0 | 24 |

(*drug deposit subcutaneous)
L $1_{LD_{50}}$ not determined since $LD_{90-100}$ was so high It is interesting to note the lack of toxicity of silver sulfadiazine when administered by the oral route. Silver sulfadiazine breaks down slowly to free silver and sulfonamide when used topically on the surface of the burn wound. At these high dose levels such a breakdown would result in the formation of silver chloride and the precipitation of proteins. Furthermore, since this compound is extremely insoluble it is interesting that this material is being absorbed into the blood stream.

The results with P. berghei show a high degree of efficacy against this malaria model. The insignificant inhibition of silver sulfadiazine's activity against this organism in the presence of very high levels of PABA indicate that its mode of action is different from that of sulfonamides. Paralleling its topcial efficacy is silver sulfadiazine's oral systemic activity against Pseudomonas aeruginosa.

II. Treatment of Neoplastic Tissue:

As indicated by Burk et al. in the Journal of the National Cancer Institute, 38:839 (1967), "On the Significance of Glucolysis for Cancer Growth With Reference to Morris Rat Hepatomas," a fundamental metabolic property of all cancer cells, even those with the lowest degree of malignancy, is the production of lactic acid from glucose under aerobic conditions. As a consequence of this activity, the pH value of neoplastic tissues assumes a lower value than that of normal tissues.

This differential in pH value can be accentuated, especially by the administration of glucose to the host. This finding of Burk et al. has been repeatedly demonstrated in animal tumors and more recently in human tumors, the latter being evidenced by Ashby in Lancet ii, 312 (1966) "pH Studies in Human Malignant Tumors."

There are various ways by which the lower pH value of tumor tissues may be exploited to produce a more selective carcinostatic agent. Thus, Stevens et al. in Science, 112:561 (1950) "Sulfapyrazine Precipitated in Cancer Tissue Upon Repeated Glucose Injections" observes that sulfapyrazine is selectively deposited in the tumor regions of glucose-treated rats bearing a transplanted Walker carcinoma.

This observation of Stevens et al. can be rationalized by taking into account the pH differences between normal and neoplastic tissues, in that suitably substituted sulfonamides are sparingly soluble in the undissociated form but yield soluble anions. This was recently demonstrated quantitatively by Calvert et al. in an article appearing in the Europ. J. Cancer 14:627 (1967) "Derivatives of Sulphanilamide Designed for Selective Deposition in Neoplastic Tissue."

If one assumes, for the sake of calculation, that cancer tissue has a pH value of 6.5 and normal tissue a pH value of 7.5, then relative solubility curves for compounds with different pKa values can be plotted as illustrated in FIG. 1 of the Calvert et al. article. FIG. 2 of this article graphically shows the percentage of the sulfonamides that is insoluble in cancer tissue divided by the percentage insoluble in normal tissue (C/N). This expression reaches a maximum for a compound with a pKa of about 5.5 and then levels out at a value of 10 as indicated by the dotted line in the graph.

However for a compound of low pKa, the percentage which is insoluble is too low for a significant deposition to take place. The optimum condition for selective deposition of an appreciable amount of the drug will be when the expression C/N X, the percentage insoluble at a given pH, reaches a maximum value in the full line curve in FIG. 2 of Calvert et al. This optimum is reached when the pKa of the drug is about 6.6. At maximum, selective deposition of sulfadiazine (pKa 6.5) and to a lesser extent sulfa thiazole (pKa 7.1) and sulfapyrazine (pKa 6.0; all in water) should occur.

Although sulfadiazine has the unusual property of concentrating selectively in the Walker tumor, it has also subsequently been shown by Connors et al. in the text "Advances in Antimicrobial and Antineoplastic Chemotherapy," Vol. II, Urban and Schwarzenberg, Munichen, 1972 (page 771), that sulfadiazine will also localize by selective concentration in other transplanted animal tumors. (Other sulfonamides such as sulfathiazole do not concentrate selectively in these tumors.)

The Connors et al. finding is of interest since most anti-tumor agents and many other chemicals (e.g., amino acids) are only poorly taken up by these tumors when compared to liver. In a typical experiment it was shown that the ratio of concentration of sulfadiazine between the Walker tumor and the liver was 5:1, while in an experiment at the same time with malphalan, which is very effective against the tumor, the ratio between the tumor and liver was 1:5. Using liver as a standard, sulfadiazine therefore concentrates in the Walker tumor twenty-five times more effectively than an active alkylating agent. Similar results were obtained for the Yoshidia sarcoma and other tumors.

As mentioned previously, the explanation put forward to explain the selective uptake of sulfadiazine by tumors is that sulfadiazine is insoluble as a free acid but very soluble when ionized. The insoluble free acid will precipitate in cells, the amount of material precipitated depending on the pKa of the agent and the intracellular pH of the cell. In tumor cells which are generally more acidic than normal cells, there will be at equilibrium more of the acidic form than in normal tissue and hence more of the insoluble form which will precipitate. Once the soluble ionized form has been excreted from the cell, there will be a depot of the precipitated material which will slowly redissolve. This finding is of only academic interest since sulfadiazine by itself is not an anti-tumor agent.

An attempt was made by Connors et al. to exploit this concept by the synthesis of a derivative of sulfadiazine containing a cytotoxic nitrogen mustard group (herein called sulfadiazine mustard or CB1954). Since this derivative had the same pKa as sulfadiazine and was insoluble as a free acid and soluble when ionized, it was expected that it would concentrate in tumors of low intracellular pH in the same way as sulfadiazine. Tests performed by Connors et al. against animal tumors showed the compound to be more effective than melphalan in some systems (Yoshidia, Walker) but not in others (PC-6 tumor). This was surprising since the PC-6 system is sensitive to akylating agents. It was subsequently shown that CB 1954 did not selectively localize, i.e., in a number of animal tumors screened, ratio between tumor and liver was 1:5 or less.

With the above background in mind, silver sulfonamides, particularly silver sulfadiazine and silver sulfamethoxydiazine were screened against the PC-6 tumor system to determine if selective localization would occur in the tumor in contradistinction to CB 1954 which was not localized. The results show that the localization of silver sulfadiazine is essentially the same as sulfadiazine itself. It was also found that the localization of silver sulfamethoxydiazine was the same as silver sulfadiazine. Silver sulfamethoxydiazine has the same pKa as silver sulfadiazine with the methoxy group in the para position of the pyrimidine ring.

Silver sulfadiazine differs from CB 1954 in that it possesses a silver atom instead of a mustard group. By the use of an appropriate radioactive silver derivative, exploitation of the localization of silver sulfadiazine is now achievable. Essentially the effects of radiation and alkylating agents are similar. The essential and highly significant difference is the reactivity of the cytotoxic component. Selectivity is not determined by the mechanism of action of a drug, but to a large extent by events that occur before and after the agent reaches its target site in the cell.

An alkylating agent must react with nuclear DNA to exert its cytotoxicity. The level of cytotoxicity will be determined by the permanent level of alkylation that occurs and this will be regulated by a number of factors such as the amount of drug entering the cell, the amount metabolized and deactivated before reaching the target site, the degree of activation of the agent if this is necessary, the concentration of nucleophilic centers in the vicinity of DNA which can divert the agent from its target site, and the ability of the cell to repair alkylated DNA before the cytotoxic effects of alkylation can occur. The use of radioactive silver sulfadiazine overcomes the problem of reactivity of a mustard group, while essentially performing the same function. (CB 1954 mustard group = di-2-chloro-n-propylaminophenyl.)

The deposition of a cytotoxic radioactive agent of appropriate chemical reactivity is advantageous for several reasons. As indicated by Hahn in "Radiochemistry of Cell Structures Containing Cycling and Non-Cycling Cells," Front. Radiation Ther. Onc. 4:17 (1969), cells are more sensitive towards alkylating agents when exposed during mitosis and the $G_1$ interphase of the mitotic cell cycle and this is a limited period of the whole cell cycle time.

Since radiation is also most effective during this stage of the cell cycle, the overall effect is similar. In a mixed cell population such as that existing in the average tumor mass, the cells will be passing through the sensitive phase at different times and it would clearly be an advantage to have an agent which could be localized in the tissue and be reactive over a considerable period. In this way an optimum effect on the whole mass could be achieved. With reference to this factor, the recent work of Skipper et al. on the effect of cytosine arabinoside on the L1210 leukemia is noted (Morgan et al., "Handbook of Radiology," p. 214 (1955) Yearbook).

By adjusting the dosage schedule so that every cell is exposed to a lethal dose of the drug during the appropriate phase, the malignant cells may be completely eradicated. Alternative dosage schedules employing even maximum tolerated doses are much less effective.

The preferred radioactive isotope used for the production of the radioactive derivatives of silver sulfadiazine and silver N'-(5-methoxy-2-pyrimidinyl) sulfanilamide, (silver sulfameter), is silver$^{111}$. This radioiostope which is essentially a pure Beta emitter has the following characteristics:

| element | isotope | half-life | max. energy | Bp mev | gamma mev | decay product |
|---------|---------|-----------|-------------|--------|-----------|---------------|
| silver  | $Ag^{111}_{47}$ | 7.5 days | 1.04 (91%)<br>0.80 ( 1%)<br>0.70 ( 8%) | | 0.25 (1%)<br>0.34 (6%) | $Cd^{111}$<br>48 |

Silver$^{111}$ has an acceptable half-life of 7.5 days, acceptable Beta particle activity and a small enough gamma emission to be practical. When the selected radioisotope is essentially a pure Beta emitter, the dose is confined to the region containing the material, at least in human beings. The range of these particles in tissue is only a few millimeters and does not project beyond the organ in that most organs are large in comparision, as indicated by Quimby et al. in "Radioactive Isotopes in Clinical Practice," Lea & Freiberger, 1958, p. 97.

While there have been shown and described preferred techniques in accordance with the invention, it will be appreciated that many changes and modifications may be made therein without, however, departing from the essential spirit thereof.

I claim:
1. A method of treating systemic infections such as malaria comprising the step of administering an aqueous suspension of insoluble silver sulfadiazine particles orally or subcutaneously in a dosage which is effective against the infection and has minimal toxicity.
2. A method as set forth in claim 1, wherein said dosage is less than 1,050 mg/kg.
3. A method of eradicating neoplastic tissue in living bodies comprising the steps of internally administering an aqueous suspension of insoluble particles consisting essentially of a radioactive derivative of silver sulfadiazine in a dosage of minimal toxicity which is sufficient to cause said particles to lodge in said tissue and eradicate same.
4. The method as set forth in claim 3, wherein the radioactive isotope used for the production of said derivative is silver$^{111}$.

* * * * *

UNITED STATES PATENT AND TRADEMARK OFFICE
CERTIFICATE OF CORRECTION

PATENT NO. : 4,020,150
DATED : April 26, 1977
INVENTOR(S) : Michael Wysor

It is certified that error appears in the above-identified patent and that said Letters Patent are hereby corrected as shown below:

Column 1, line 25 "sulfur" should have read -- sulver --.

Column 3, line 19 "Doese" should have read -- Doses --

Column 4, line 45 "topcial" should have read -- topical --

Column 8, line 4 "parision" should have read -- parison --

Signed and Sealed this thirtieth Day of August 1977

[SEAL]

Attest:

RUTH C. MASON
Attesting Officer

C. MARSHALL DANN
Commissioner of Patents and Trademarks